US 6,599,520 B2

(12) United States Patent
Scarborough et al.

(10) Patent No.: US 6,599,520 B2
(45) Date of Patent: Jul. 29, 2003

(54) METHOD OF INDUCING NEW BONE GROWTH IN POROUS BONE SITES

(75) Inventors: Nelson L. Scarborough, Andover, MA (US); James Russell, Little Silver, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 10/100,475

(22) Filed: Mar. 14, 2002

(65) Prior Publication Data

US 2002/0132012 A1 Sep. 19, 2002

Related U.S. Application Data

(63) Continuation of application No. PCT/US00/28376, filed on Oct. 13, 2000.
(60) Provisional application No. 60/159,402, filed on Oct. 14, 1999.

(51) Int. Cl.$^7$ .................................................. A61F 2/00
(52) U.S. Cl. ......................................................... 424/426
(58) Field of Search ............................ 424/426; 523/114, 523/115

(56) References Cited

U.S. PATENT DOCUMENTS 5,922,753 A  *  7/1999  Petrie et al.

* cited by examiner

*Primary Examiner*—Carlos A. Azpuru
(74) *Attorney, Agent, or Firm*—Dilworth & Barrese, LLP

(57) ABSTRACT

A method of treating a condition in a vertebrate animal characterized by bone having increased porosity and/or decreased bone mineral density. The porous bone is injected with an effective amount of a flowable bone composition. Also provided is a kit for the treatment of porous bone wherein a flowable bone composition is contained within an injectable delivery system.

25 Claims, No Drawings

METHOD OF INDUCING NEW BONE GROWTH IN POROUS BONE SITES

This application is a continuation of PCT/US00/28376, filed Oct. 13, 2000, and claims the benefit of Provisional application Ser. No. 60/159,402, filed Oct. 14, 1999.

BACKGROUND OF INVENTION

This invention relates to methods for the treatment of porous bone, e.g., osteoporotic bone. The expression "porous bone" is intended herein to identify a condition of porosity and/or decreased bone mineral density that distinguishes the morphology of bone exhibiting a pathological condition from healthy bone. A common type of porous bone pathology is osteoporosis.

Osteoporosis is a pathologic state or disease involving some symptom or risk due to quantitative bone reduction exceeding a certain degree. Major symptoms are spinal kyphosis, fractures of dorsolumbar bones, vertebral centra, femoral necks, lower ends of radius, ribs, upper end of humerus, and others. In normal bone tissue, bone breakdown occurs constantly, but there is good balance between formation and resorption; osteoblasts and osteoclasts play key roles in bone formation and bone resorption, respectively. Upon deterioration of this balance, bone resorption surpasses bone formation, resulting in quantitative bone reduction.

Osteoporosis results in bone fractures in about 50% of postmenopausal women and is a leading cause of disability in an aging population. The decrease in bone mineral density and changes in architecture that accompany postmenopausal osteoporosis predisposes elderly women to fractures, particularly of the vertebral bodies. It is not elderly persons alone who suffer from this painful condition. Other individuals, such as transplant recipients, suffer fractures as a result of chronic steroid use. Current therapies include an adequate calcium and vitamin D intake as well as specific treatment with compounds such as estrogens, calcitonin and the bisphosphonates. However, each of these treatments has either troubling side effects or limited efficacy. Women fear the small increase in potential risk of breast cancer due to estrogens despite the dramatic reduction in myocardial infarctions and reduction in bone resorption. Calcitonin has a limited effect and is a protein and therefore needs to be injected or inhaled which is inconvenient. The new bisphosphonates such as alendronate have had encouraging results with an increase in bone density and decrease in fractures, however, some upper gastrointestinal irritation has been reported (Abraham et al., 1999, Mod. Pathol. Dec 12(12): 1152–1157). Current research for new compounds has concentrated on the systemic administration of bone anabolic compounds such as parathyroid hormone (PTH) or fragments of PTH or locally acting cytokines or bone growth factors such as bone morphogenic proteins. When these therapies are unable to prevent fractures of porous bone, the victims of such fractures suffer from persistent, often excruciating pain, which significantly impairs mobility and quality of life. External bracing, analgesics, and observation may be all that is necessary for pain control in some patients, but in others, a constant requirement for narcotics can be as life altering as the fracture itself.

Vertebroplasty has been described in the literature as a method of injecting materials into vertebral bodies via a pedicle approach. Patients with various problems including osteoporosis, tumor or trauma have deficiencies of the vertebral body leading to pain or other complications. By injecting methylmethacrylate (bone cement) into these areas interventional radiologists or other physicians are able to avoid further subsidence of the vertebrae and alleviate pain. This procedure can be done on an outpatient basis, but currently is reserved for patients with major problems. The current methods of vertebroplasty are directed toward treatment once a fracture occurs. Therefore, a prophylactic treatment directed toward reducing the tendency for porous vertebrae to fracture would be highly desirable This invention describes the use of a flowable bone graft composition to induce bone growth at porous bone sites. A suitable bone graft for this indication would have the properties of flowability. i.e., allowing for injection through a 2–6 mm or larger trocar, and ability to support formation of new bone at the porous bone site. An ideal material would be flowable DBM (with or without enhancing substances such as BMP) such as that disclosed in U.S. Pat. Nos. 5,073,373, 5,236,456, 5,314,476, 5,405,390, 5,484,601 and 5,510,396 and commonly assigned PCT/US00/28462, filed Oct. 13, 2000, the contents of all of which are incorporated herein by reference.

BRIEF SUMMARY OF THE INVENTION

It is an object of the invention to provide a method of treating a vertebrate animal having increased bone porosity and/or decreased bone mineral density.

It is a further object of the invention to provide a method for treating osteoporotic patients at risk for fracture of the vertebra or other sites.

It is a further object of the invention to provide a method for increasing the bone mineral density and/or decreasing bone porosity thereby decreasing the risk for future fracture.

It is a further object of the invention to provide a method of treating at risk vertebrae adjacent to a fractured vertebra.

The stated objects of the invention are not intended to be limiting in any way. Of course, further objects of the invention herein will be obvious to those skilled in the art in view of the above stated objects and the foregoing specification.

In keeping with these and related objects of the invention, there is provided a method of treating a condition in a vertebrate animal, the condition characterized by bone having increased porosity and/or decreased bone mineral density, which comprises injecting the porous bone with an effective amount of a flowable bone composition. The foregoing method applied to a site of increased bone porosity and/or decreased bone mineral density, e.g., one resulting from disease, malignancy or developmental malformation, leads to rapid new bone ingrowth by one or more mechanisms such as osteogenesis, osteoconduction and osteoinduction. The method of this invention is relatively simple, e.g., it can be performed on an outpatient basis, and relatively inexpensive, and avoids the major complications caused by vertebral fracture.

DETAILED DESCRIPTION OF THE INVENTION

The method described herein is performed on individuals identified as being at risk for bone fracture due to increased bone porosity and/or decreased bone mineral density. Such individuals are identified using methods well known in the art, e.g., bone density scans, radiographic imaging, medical history. The conditions leading to decrease in bone density can include, e.g., osteoporosis, osteomalacia, osteotis fibrosa, Paget's disease, bone deficiency, primary or secondary hyperparathyroidism, chronic inflammatory conditions, metastatic bone disease and osteolytic bone disease. When the condition is osteoporosis, the osteoporosis can be due to a number of conditions, e.g., age-related osteoporosis, post-menopausal osteoporosis, juvenile osteoporosis, Cushing's syndrome osteoporosis, multiple myeloma osteoporosis, leukemia osteoporosis, Turner's syndrome osteoporosis, alcohol osteoporosis, chronic liver disease osteoporosis, glucocorticoid-induced osteoporosis, chronic inflammatory disease induced osteoporosis and disuse osteoporosis. The site of decreased bone density can be trabecular bone, cortical bone, etc. When the bone site is trabecular bone the bone can include, e.g., vertebrae, rib, clavicle, sternum, femoral neck, hip, wrist and the distal ends of the long bones.

Once the site of decreased bone density is located utilizing methods well known in the art, e.g., bone density scans, radiographic imaging, medical history, a suitable amount of a flowable bone composition is injected into the bone site utilizing methods well known in the art, e.g., through a needle or cannula, e.g., a Jamshidi®11 gauge bone marrow biopsy/aspiration needle. In a preferred embodiment of the invention, a percutaneous vertebroplasty technique as described by Jensen et al. *Diagnostic Imaging*, pp. 68–72, September 1997, the contents of which are incorporated herein by reference, is used to inject the osteoinductive composition into the vertebra. This technique, a fluoroscopically guided transpedicular approach, has been found to be the easiest, safest and least time-consuming.

The bone component of the composition herein is a known type of material and is prepared in accordance with known procedures. The expressions "pulverized bone", "powdered bone", "bone particles" and "bone powder" as used herein shall be understood to include bone particles of a wide range of average particle size ranging from relatively fine powders to coarse grains and even larger chips or fibers. So, for example, the bone component present in the composition of this invention can range in average particle size from about 0.1 to about 1.2 cm and preferably from 0.2 to 1 cm. Bone particles whose median length to median thickness is at least about 10:1 are also suitable for use in the bone component useful herein. The bone component can be obtained from cortical, cancellous and/or corticocancellous allogenic, xenogenic or transgenic bone tissue. In general, allogenic bone tissue is preferred as the source of the bone component. The bone component may be mineralized, partially demineralized or demineralized as well as combinations thereof. Of course, it will be understood that any combination of the above-identified bone can be used in the preparation of flowable bone compositions useful in the practice of the invention herein.

In a preferred bone demineralization procedure, the bone is first pulverized to the desired average particle size followed by defatting/disinfecting and acid demineralization treatments. A preferred defatting/disinfectant solution, for example, is an aqueous solution of ethanol, the ethanol being a good solvent for lipids and the water being a good hydrophilic carrier to enable to solution to penetrate more deeply into the bone. The aqueous ethanol solution also disinfects the bone by killing vegetative microorganisms and viruses. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is, for example, about 60% to 85% alcohol and most preferably 70% alcohol. Following defatting, the bone is immersed in acid over time to effect demineralization. Acids which can be employed in this operation include, for example, inorganic acids such as hydrochloric acid and organic acids such as peracetic acid. After acid treatment, the bone component is rinsed with water for injection, buffered with a buffering agent to a final predetermined pH and then finally rinsed with water for injection to remove residual amounts of acid and buffering agent. The demineralized bone component can be used immediately for preparation of the composition of this invention or it can be stored under aseptic conditions, advantageously in a freeze-dried state, prior to such preparation.

If desired, the bone component can be modified in one or more ways, e.g., the porosity of the bone component can be increased and/or the bone component can be treated with one or more modifying agents, e.g., gluturaldehyde, as disclosed in U.S. Pat. No. 4,678,470 the contents of which are incorporated herein by reference. Another optional treatment involves the augmentation of the bone protein content of the bone employing the procedure of U.S. Pat. Nos. 4,743,259 and 4,902,296 the contents of which are incorporated herein by reference. Any of a variety of medically and/or surgically useful substances can be incorporated in, or associated with, the bone component before, during, or after preparation of the osteoinductive composition. Thus, e.g., one or more of such substances can be introduced into the bone component, e.g., by soaking or immersing the bone component in a solution or dispersion of the desired substance(s), by adding the substance(s) to the carrier component of the osteoinductive composition of by adding the substances directly to the osteoinductive composition. Broad classifications of such substances would include, for example, agents that promote bone growth and/or inhibit bone resorption, e.g., bone morphogenetic factors, anti-resorption agents, osteogenic factors, cartilage-derived morphogenetic proteins, hormones, growth hormones and differentiating factors.

Medically/surgically useful substances, which can be readily combined with the bone component, fluid carrier and/or osteoinductive composition of this invention, include, e.g., demineralized bone powder as described in U.S. Pat. No. 5,073,373 the contents of which are incorporated herein by reference, all collagen types (not just type I), insoluble collagen derivatives, non-collagenous proteins such as osteopontin, osteonectin, bone sialo proteins, vitronectin, thrombospondin, proteoglycans, decorin, biglycan, aggrecan, veriscan, tenascin, matrix gla protein hyaluronan; hydroxyapatite, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin, etc.; amino acids, peptides, vitamins, inorganic elements, inorganic compounds, cofactors for protein synthesis, hormones; soluble and insoluble components of the immune system, soluble and insoluble receptors including truncated forms, soluble, insoluble and cell surface bound ligands including truncated forms; chemokines, bioactive compounds that are endocytosed; endocrine tissue or tissue fragments; synthesizers; enzymes such as collagenase, peptidases, oxidases, etc.; polymer cell scaffolds with paraenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1) (IGF-2), platelet derived growth factor (PDGF), fibroblast growth factors (FGF), vascular endothelial growth factor (VEGF), epidermal growth factor (EGF), angiogenic agents, bone promoters, cytokines, interleukins, genetic material, genes encoding bone promoting action, cells containing genes encoding bone promoting action; hormones, growth hormones such as somatotropin; bone digestors; antitumor agents; fibronectin; cellular attractants and attachment agents; immuno-suppressants; bone resorption inhibitors and stimulators; angiogenic and mitogenic factors; bioactive factors that inhibit and stimulate second messenger molecules; cell-matrix and cell-cell adhesion molecules; clotting factors; externally expanded autograft or xenograft cells, permeation enhancers, e.g., fatty acid esters such as laureate, myristate and stearate monesters of polyethylene glycol, enamine derivatives, α-keto aldehydes, etc.; and, nucleic acids and any combination thereof. The amounts of such optionally added substances can vary widely with optimum levels being readily determined in a specific case by routine experimentation.

The flowable bone composition can be modified to increase its suitability for this application. It can be rendered radiopaque by the addition of compositions containing barium, tungsten or mineralized bone. Optionally, agents that inhibit bone mineral loss or depress bone turnover can be added to the composition. Such agents include, for example, stable active analogs of pyrophosphate such as those known as bisphosphonates and estrogen and analogs thereof.

To provide the flowable bone composition useful in the practice of the invention herein, the bone component with or without any of the foregoing optional components mentioned above absorbed therein is combined with a biocompatible liquid organic material which functions as a carrier or suspension agent for the bone component.

The term "liquid" as employed herein is intended to include (1) organic materials which in the pure or highly concentrated state and at ambient temperature, e.g., 15 degree–40 degree C., are flowable liquids and (2) organic materials which in the pure or concentrated state and at ambient temperature are normally solid but dissolved in a suitable solvent, e.g., water or a biocompatible organic solvent such as ethanol, can be provided in liquid form. Functionally, the liquid component of the composition serves to provide a flowable material of widely varying consistency. The term "flowable" as used herein applies to compositions whose consistency range from those that can be described as shape-sustaining but readily deformable, e.g., those that behave like putty, to those which are runny. Specific forms of flowable bone compositions include cakes, pastes, putties, creams, fillers and gels. Suitable carriers can be any of a number of compounds and/or polymers, e.g., polymer sugars, proteins, long chain hydrophilic block copolymers, reverse phase block copolymers, hyaluronic acid, polymonic acid, mucopolysaccharide, proteoglycan, polyoxyethylene, surfactants, e.g., the Pluronics series of nonionic surfactants, and peptide thickener. Suggested classes of biocompatible fluid carrier would include polyhydroxy compound, polyhydroxy ester, fatty alcohol, fatty alcohol ester, fatty acid, fatty acid ester, liquid silicone, mixtures thereof, and the like. Examples of suitable biocompatible fluid carrier include, but are not limited to:

(i) Polyhydroxy compound, for example, such classes of compounds as the acyclic polyhydric alcohols, non-reducing sugars, sugar alcohols, sugar acids, monosaccarides, disaccharides, water-soluble or water dispersible oligosaccarides, polysaccarides and known derivatives of the foregoing. Specific polyhydroxy compounds include 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, e.g., of the type known and commercially available under the trade names Pluronic and Emkalyx; polyoxyethylene-polyoxypropylene block copolymer, eg., of the type known and commercially available under the trade name Poloxamer; alkylphenolhydroxypolyoxyethylene, e.g., of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

(ii) Polyhydroxy ester, for example, liquid and solid monoesters and diesters of glycerol can be used to good effect, the solid esters being dissolved up to the limit of their solubilities in a suitable vehicle, e.g., propylene glycol, glycerol, polyethylene glycol of 200–1000 molecular weight, etc., Liquid glycerol esters include monacetin and diacetin and solid glycerol esters include such fatty acid monoesters of glycerol as glycerol monolaurate, glyceryl monopalmitate, glyceryl monostearate, etc. An especially preferred carrier herein comprises glyceryl monolaurate dissolved in glycerol or a 4:1 to 1:4 weight mixture of glycerol and propylene glycol, poly (oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid. (vi) Fatty acid ester, for example, polyoxyethylene-sorbitan-fatty acid esters; e.g., mono-and tri-lauryl, palmityl, stearyl, and oleyl esters; e.g., of the type available under the trade name Tween from Imperial Chemical Industries; polyoxyethylene fatty acid esters; e.g., polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol; e.g., of the type known and commercially available under the trade name Imwitor; sorbitan fatty acid esters, e.g., of the type known and commercially available under the trade name Span, including sorbitan-monolauryl, -monopalmityl, -monostearyl, -tristearyl, -monooleyl and trioleylesters; monoglycerides, e.g., glycerol mono oleate, glycerol mono palmitate and glycerol monostearate, for example as known and commercially available under the trade names Myvatex, Myvaplex and Myverol, and acetylated, e.g., mono- and di-acetylated monoglycerides, for example as known and commercially available under the trade name Myvacet; isobutyl tallowate, n-butylstearate, n-butyloleate, and n-propyloleate.

(vi) Liquid silicone, for example, polyalkyl siloxanes such as polymethyl siloxane and poly (dimethyl siloxane) and polyalkyl arylsiloxane.

In a preferred embodiment of the osteoinductive composition, the liquid carrier is a liquid polyhydroxy compound, liquid polyhydroxy compound derivative, liquid solution of solid polyhydroxy compound, liquid solution of solid polyhydroxy compound derivative or mixtures thereof. If necessary or desirable, the liquid carrier can be dissolved or diluted with an appropriate solvent such that when combined with the demineralized bone particles of the invention a readily flowable composition is provided. Thus, the polyhydroxy compound or polyhydroxy derivatives can be a liquid in the pure or highly concentrated state at ambient temperature, e.g., 1.5–50° C., or it can be a solid or semi-solid at this temperature in which case it becomes necessary to dissolve the material in a solvent such as water, physiological saline, ethanol, glycerol, glucose, propylene glycol, polyethylene glycol of from 200–1000 molecular weight, polyvinyl alcohol, etc. Of course, the liquid carrier can be made up of one or more liquid polyhydroxy compounds or derivatives in solution with one or more solid polyhdroxy compounds or derivatives.

Of the foregoing polyhydroxy compounds, glycerol and its liquid monesters and diesters, e.g. monacetin and diacetin, fructose, glucose and sucrose, and mixtures thereof are preferred. Where the polyhydroxy compound is a solid, e.g., sucrose, a solvent such as water, glycerol, polyethylene glycol of from 200–1000 average molecular weight, or mixture thereof is used to provide a cohesive solution or paste of the compound.

Where, in a particular osteoinductive composition, the bone component exhibits a tendency to quickly or prematurely separate from the carrier component or to otherwise settle out from the composition such that application of a fairly homogeneous composition is rendered difficult or inconvenient, it can be advantageous to include within the composition a substance whose thixotropic characteristics prevent or reduce this tendency. Thus, e.g., where the carrier component is glycerol and separation of the component occurs to an excessive extent where a particular application is concerned, a thickener such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the carrier in an amount sufficient to significantly improve the suspension-keeping characteristics of the composition.

As previously indicated, the bone composition of this invention can be freshly prepared just prior to use by mixing of the bone component, carrier and optional component(s) in any suitable sequence of separate mixing operations or all at once. Thus, the bone component can be mixed with the optional ingredient(s) and thereafter combined with the liquid carrier component, the bone component can be mixed with the carrier followed by addition of the optional ingredient(s) or the optional ingredients can be added to the carrier followed by addition of the bone component. Variations of these sequences of mixing operations are of course, possible. The amount of bone component which can be incorporated into the composition of this invention can vary widely with amounts of from about 5 to 80 weight percent, and preferably from about 20 to about 65 weight percent, being entirely suitable in most cases. To facilitate on-site preparation of the composition herein, the bone component, preferably in lyophilized form, and carrier (the latter, containing any of the optional ingredients identified above) can be stored in separate packages or containers under sterile conditions and brought together in intimate admixture at the moment of use for immediate application to a bone defect site employing any suitable means, e.g., a syringe and cannula. U.S. Pat. No. 4,458,733, the contents of which are incorporated by reference herein, describes a combined storage, mixing and application device that can be adapted to perform the foregoing functions of storage, mixing and application. Alternatively, the bone composition can be prepared well in advance and stored under sterile conditions until required for use, e.g., in the barrel of a syringe or other suitable applicator device. In a preferred embodiment, the flowable demineralized bone powder composition of this invention is packaged in kit form to facilitate the treatment of porous bone.

The following examples are illustrative of the preparation of a preferred flowable bone composition useful in the practice of the invention herein and its use to treat osteoporotic vertebrae. The examples are intended to illustrate certain preferred embodiments of the invention but are not intended to limit the practice of the invention as disclosed by the specification and set forth in the claims herein.

EXAMPLE I

A quantity of allogenic cortical or cancellous bone that has been pulverized and sieved to an average particle size of from about 100 to about 300 microns is introduced into a reactor that is then sealed. A 70% ethanol solution at the rate of 30 milliliters per gram of bone is introduced into the reactor followed by agitation for 1 hour (Bolander et al., Journal of Bone and Join Surgery, Vol. 68-A, No. 8 (October 1986) to effect defatting and disinfecting of the bone powder. Following drainage of the ethanol, a 0.6 N solution of HCl at a rate of 50 ml per gram of bone is introduced into the reactor (Bolander et al., ibid.), the reaction proceeding for 3 hours (Glowackie, AATB Workshop, 11$^{th}$ Annual meeting (1987)). Following drainage of the HCl, the bone is covered and rinsed three times with water for injection (WFI) with the WFI being replaced at 5-minute intervals. Following drainage of the WFI, the bone is completely covered with 0.1M sodium phosphate, a procedure which is repeated until the pH of the solution falls between 6.8 and 7.4. The rinsing procedure with WFI is repeated to provide demineralized cortical or cancellous bone powder ready for mixing with the carrier component to provide the flowable composition of this invention.

The foregoing demineralized bone powder, 2.5 gm, and injectable grade glycerol, 9.5 gm, is thoroughly mixed to provide a composition of pastelike consistency. The composition is readily applied to a bone defect site, e.g. employing a syringe or spatula.

EXAMPLE II

The site of decreased bone density is located utilizing methods well known in the art, e.g., bone density scans, radiographic imaging, medical history. Then, a flowable bone composition is injected into the bone site utilizing methods well known in the art, e.g., through a needle or canula, e.g., a Jamshidi® 11 gauge bone marrow biopsy/aspiration needle. When the bone to be treated is a vertebra, the vertebra is accessed utilizing methods well known into the art, e.g. endoscopically or percutaneously. In a preferred embodiment of the invention a percutaneous vertebroplasty technique as described by Jensen et al. *Diagnostic Imaging*, pp. 68–72, September 1997, is used to inject the osteoinductive composition into the vertebra. This technique is a fluoroscopically guided transpedicular approach that has been found to be the easiest, safest and least time-consuming. The procedure is done under strict sterile conditions; operators wear surgical caps and masks in addition to sterile gowns and gloves. All team members and observers in the room also wear surgical caps and masks to minimize contamination of the materials. With the patient prone, the vertebral body to be treated is localized and overlying skin is prepped and draped in a sterile fashion. As the transpedicular approach is used, one of the pedicles is isolated, and the anteroposterior tube is angled such that a "looking down the barrel" appearance is attained. The skin, subcutaneous soft tissue and periosteum are anesthetized, and a small skin incision is made. The pedicle is traversed using an 11-G bone biopsy needle, and the needle position in both planes is checked frequently. Once the needle tip is located in the midportion of the vertebral body, contrast is injected with filming in both planes. After the needle position is confirmed, the composition is either mixed or the premixed composition is used and injected in 1-cc aliquots into the bone. Filling is complete when no more composition can be injected. In some patients, the composition will migrate across the mid line to fill both vertebral hemispheres, but in most cases a puncture of the contralateral pedicle must also be made. More than one level can be treated at the same sitting.

What is claimed is:

1. A method of treating a condition in a vertebrate animal, the condition characterized by a bone having increased porosity and/or decreased bone mineral density, which comprises injecting the bone with an effective amount of a flowable bone composition, the bone being selected from the group consisting of trabecular bone and cortical bone.

2. The method of claim 1 wherein the trabecular bone is selected from the group consisting of vertebrae, rib, clavicle, sternum, femoral neck, hip, wrist and the distal ends of the long bones.

3. The method of claim 1 wherein the condition is selected from the group consisting of osteoporosis, osteomalacia, osteitis fibrosa, Paget's disease, bone deficiency, primary or secondary hyperparathyroidism, chronic inflammatory conditions, metastatic bone disease and osteolytic bone disease.

4. The method of claim 3 wherein the condition of osteoporosis is selected from the group consisting of age-related osteoporosis, post-menopausal osteoporosis, juvenile osteoporosis, Cushing's syndrome osteoporosis, multiple myeloma osteoporosis, leukemia osteoporosis, Turner's syndrome osteoporosis, alcohol osteoporosis, chronic liver disease osteoporosis, glucocorticoid-induced osteoporosis, chronic inflammatory disease induced osteoporosis and disuse osteoporosis.

5. The method of claim 1 further comprising administering to the animal one or more agents that promote bone growth and/or inhibit bone resorption.

6. The method of claim 5 wherein the agent(s) is selected from the group consisting of bone morphogenetic factors, anti-resorption agents, osteogenic factors, cartilage-derived morphogenetic proteins, hormones, growth hormones, genetic material and differentiating factors.

7. A method of vertebroplasty which comprises injecting a vertebra having increased porosity and/or decreased bone mineral density with an effective amount of flowable bone composition, the bone being selected from the group consisting of trabecular bone and cortical bone.

8. The method of claim 7 wherein the bone is selected from the group consisting of vertebrae, rib, clavicle, sternum, femoral neck, hip, wrist and the distal ends of the long bones.

9. The method of claim 7 further comprising administering to the animal one or more agents that promote bone growth and/or inhibit bone resorption.

10. The method of claim 9 wherein the agent(s) is selected from the group consisting of bone morphogenetic factors, anti-resorption agents, osteogenic factors, cartilage-derived morphogenetic proteins, hormones, growth hormones, genetic material and differentiating factors.

11. The method of claim 1 wherein the bone is provided as a mass of particles ranging in average size from about 0.1 to about 1.2 cm.

12. The method of claim 11 wherein the bone particles are selected from the group consisting of mineralized bone particles, partially demineralized bone particles, demineralized bone particles and combinations thereof.

13. The method of claim 1 wherein the flowable bone composition includes a biocompatible liquid material as carrier or suspension agent for the bone.

14. The method of claim 13 wherein the biocompatible liquid material is glycerol or glycerol solution.

15. The method of claim 7 wherein the bone is provided as a mass of particles ranging in average size from about 0.1 to about 1.2 cm.

16. The method of claim 15 wherein the bone particles are selected from the group consisting of mineralized bone particles, partially demineralized bone particles, demineralized bone particles and combinations thereof.

17. The method of claim 7 wherein the flowable bone composition includes a biocompatible liquid material as carrier or suspension agent for the bone.

18. The method of claim 17 wherein the biocompatible liquid material is glycerol or glycerol solution.

19. A method of treating a condition in a vertebrate animal, the condition characterized by a bone having increased porosity and/or decreased bone mineral density, which comprises injecting the bone with an effective amount of a flowable bone composition, the bone being selected from the group consisting of cortical bone and trabecular bone selected from the group consisting of vertebrae, rib, clavicle, sternum, femoral neck, hip, wrist and the distal ends of the long bones.

20. A method of treating a condition in a vertebrate animal, the condition characterized by a bone having increased porosity and/or decreased bone mineral density, which comprises injecting the bone with an effective amount of a flowable bone composition, the bone being selected from the group consisting of trabecular bone and cortical bone, wherein the flowable bone composition is provided as a mass of particles ranging in average size from about 0.1 to about 1.2 cm.

21. The method of claim 20 wherein the bone particles are selected from the group consisting of mineralized bone particles, partially demineralized bone particles, demineralized bone particles and combinations thereof.

22. A method of treating a condition in a vertebrate animal, the condition characterized by a bone having increased porosity and/or decreased bone mineral density, which comprises injecting the bone with an effective amount of a flowable bone composition, the bone being selected from the group consisting of trabecular bone and cortical bone, wherein the flowable bone composition includes a biocompatible liquid material selected from the group consisting of glycerol and glycerol solution as carrier or suspension agent for the flowable bone composition.

23. A method of vertebroplasty which comprises injecting a vertebra having increased porosity and/or decreased bone mineral density with an effective amount of flowable bone composition, the bone being selected from the group consisting of trabecular bone and cortical bone, wherein the flowable bone composition is provided as a mass of particles ranging in average size from about 0.1 to about 1.2 cm.

24. The method of claim 23 wherein the bone particles are selected from the group consisting of mineralized bone particles, partially demineralized bone particles, demineralized bone particles and combinations thereof.

25. A method of vertebroplasty which comprises injecting a vertebra having increased porosity and/or decreased bone mineral density with an effective amount of flowable bone composition, the bone being selected from the group consisting of trabecular bone and cortical bone, wherein the flowable bone composition includes a biocompatible liquid material selected from the group consisting of glycerol and glycerol solution as carrier or suspension agent for the flowable bone composition.

* * * * *